United States Patent [19]
Ramin

[11] Patent Number: 6,099,826
[45] Date of Patent: *Aug. 8, 2000

[54] USE OF CERAMIDE FOR THE TREATMENT OF NAILS

[75] Inventor: Roland Ramin, Itteville, France

[73] Assignee: L'Oreal, France

[*] Notice: This patent issued on a continued prosecution application filed under 37 CFR 1.53(d), and is subject to the twenty year patent term provisions of 35 U.S.C. 154(a)(2).

[21] Appl. No.: 08/844,612

[22] Filed: Jul. 21, 1997

[30] Foreign Application Priority Data

Apr. 22, 1996 [FR] France ................................. 96 05022

[51] Int. Cl.⁷ ............................... A61K 6/00; A61K 7/00; A61K 7/04
[52] U.S. Cl. .............................................. 424/61; 424/401
[58] Field of Search ........................................ 424/61, 401

[56] References Cited

U.S. PATENT DOCUMENTS

| | | | |
|---|---|---|---|
| 5,415,855 | 5/1995 | Critchley et al. | 424/61 |
| 5,476,661 | 12/1995 | Pillai et al. | 424/401 |
| 5,582,832 | 12/1996 | Pillai et al. | 424/401 |

FOREIGN PATENT DOCUMENTS

| | | |
|---|---|---|
| 0 587 288 | 7/1993 | European Pat. Off. . |
| 0 608 600 | 9/1993 | European Pat. Off. . |
| 0 647 617 | 10/1994 | European Pat. Off. . |
| 0 679 383 | 3/1995 | European Pat. Off. . |
| WO 92/06982 | 10/1991 | WIPO . |

*Primary Examiner*—Thurman K. Page
*Assistant Examiner*—Sharon Howard
*Attorney, Agent, or Firm*—Finnegan, Henderson, Farabow, Garrett & Dunner, L.L.P.

[57] ABSTRACT

A process for the cosmetic treatment of the nails comprising the step of including at least one compound of ceramide type in a cosmetic composition.

19 Claims, No Drawings

USE OF CERAMIDE FOR THE TREATMENT OF NAILS

The present invention relates to the use, in a cosmetic composition, of at least one compound of ceramide type for the cosmetic treatment of the nails.

It is well known that the nails often have structural and consistency defects, these possibly being of diverse origin and, in particular, associated with the individual's internal functioning, his living conditions, his eating habits, his age and his states of fatigue or of overwork.

These defects may also appear under the effect of eroding actions, for example following prolonged or repeated exposure to detergents, to solvents, to chemical products, in particular household products, to humid or dry, hot or cold atmospheres, or to exposure to UV radiation.

These structural and consistency defects have the effect of making the surface of the nails look unpleasant, which may be a source of irritation and of much displeasure.

In order to strengthen the nails, various types of compositions based essentially on the use either of protein-crosslinking agents designed to strengthen the keratin network such as, for example, formaldehyde, or of agents having an essentially nutrient function such as, for example, cystine, cholesterol, S-carboxymethylcysteine or collagen extracts, have already been proposed.

However, the use of such crosslinking agents or of such agents having a nutrient function does not make it possible to obtain good results and moreover presents certain drawbacks. In particular, formaldehyde-based products may give rise to certain allergic reactions.

The inventor has observed, surprisingly and unexpectedly, that by using compounds of ceramide type, it is possible to improve the surface state of the nails. In particular, the outer surface of nails treated by application of a composition comprising a compound of ceramide type makes it possible to obtain a more uniform outer surface of the nail: the nail becomes smoother and shinier.

The subject of the present invention is thus the use, in a cosmetic composition, of at least one compound of ceramide type in order to make the outer surface of the nails uniform.

In particular, the ceramide may improve the smooth and/or shiny nature of the outer surface of the nails.

The application of ceramides to the nails in accordance with the invention is particularly advantageous for the treatment of striated nails. It is noted that the treatment of such nails makes it possible to obtain a good improvement of the outer surface of the nail since this treated surface is considerably more uniform.

The term "make the outer surface of the nail uniform" is understood to mean that the compound of ceramide type forms a uniform deposit by adsorption on the outer surface of the nail. Without being bound by the present explanation, it may be envisaged that this is due to the fact that the ceramide diffuses and penetrates into the intercellular spaces of the nails, resulting in smoother and shinier nails.

According to the present invention, the expression compound of ceramide type is understood to refer to ceramides and/or glycoceramides and/or pseudoceramides. They are preferably chosen from natural or synthetic molecules corresponding to formula (I) below:

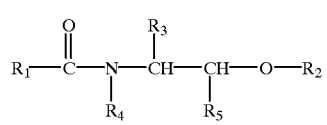

in which:
$R_1$ denotes:
either a saturated or unsaturated, linear or branched $C_1$–$C_{50}$, preferably $C_5$–$C_{50}$ and more preferably $C_9$–$C_{30}$, hydrocarbon radical, it being possible for this radical to be substituted with one or more hydroxyl groups which are optionally esterified with an acid $R_7COOH$, $R_7$ being an optionally mono- or polyhydroxylated linear or branched, saturated or unsaturated $C_1$–$C_{35}$, and preferably $C_{16}$–$C_{30}$, hydrocarbon radical, it being possible for the hydroxyl or hydroxyls of the radical $R_7$ to be esterified with an optionally mono- or polyhydroxylated, linear or branched, saturated or unsaturated $C_1$–$C_{35}$ fatty acid, or a radical R"—(NR—CO)—R', wherein R denotes a hydrogen atom or a mono- or polyhydroxylated, preferably monohydroxylated, $C_1$–$C_{20}$, preferably $C_1$–$C_{10}$, hydrocarbon radical, R' and R" are hydrocarbon radicals, the sum of whose carbon atoms ranges from 9 to 30, R' being a divalent radical, or a radical $R_8$—O—CO—$(CH_2)_p$, wherein $R_8$ denotes a $C_1$–$C_{20}$ hydrocarbon radical, p being an integer ranging from 1 to 12;

$R_2$ is chosen from a hydrogen atom, a radical of saccharide type, in particular a (glycosyl)$_n$, (galactosyl)$_m$ or sulphogalactosyl radical, a sulphate or phosphate residue, a phosphorylethylamine radical and a phosphorylethylammonium radical, in which n is an integer ranging from 1 to 4 and m is an integer ranging from 1 to 8;

$R_3$ denotes a hydrogen atom or a $C_1$–$C_{33}$, preferably $C_{16}$–$C_{27}$, saturated or unsaturated, hydroxylated or non-hydroxylated hydrocarbon radical, it being possible for the hydroxyl or hydroxyls to be esterified with an inorganic acid or an acid $R_7COOH$, $R_7$ having the same meanings as above, it being possible for the hydroxyl or hydroxyls to be etherified with a (glycosyl)$_n$, (galactosyl)$_m$, wherein m and n are as defined above, sulphogalactosyl, phosphorylethylamine or phosphorylethylammonium radical, it also being possible for $R_3$ to be substituted with one or more $C_1$–$C_{14}$ alkyl radicals; preferably, $R_3$ denotes a $C_{15}$–$C_{26}$ α-hydroxyalkyl radical, the hydroxyl group optionally being esterified with a $C_{16}$–$C_{30}$ α-hydroxy acid $R_4$ denotes a hydrogen atom, a methyl or ethyl radical, an optionally hydroxylated linear or branched, saturated or unsaturated $C_3$–$C_{50}$, preferably $C_{16}$–$C_{27}$, hydrocarbon radical or a radical —$CH_2$—CHOH—$CH_2$—O—$R_6$ in which $R_6$ denotes a $C_{10}$–$C_{26}$ hydrocarbon radical or a radical $R_8$—O—CO—$(CH_2)_p$, wherein $R_8$ denotes a $C_1$–$C_{20}$ hydrocarbon radical, and p is an integer ranging from 1 to 12, $R_5$ denotes a hydrogen atom or an optionally mono- or polyhydroxylated linear or branched, saturated or unsaturated $C_1$–$C_{30}$ hydrocarbon radical, it being possible for the hydroxyl or hydroxyls to be etherified with a (glycosyl)$_n$, (galactosyl)$_m$, wherein m and n are as defined above, sulphogalactosyl, phosphorylethylamine or phosphorylethylammonium radical; preferably, $R_5$ denotes a linear or branched, saturated or unsaturated $C_1$–$C_4$ hydrocarbon radical, with the proviso that when $R_3$ and $R_5$ denote hydrogen or when $R_3$ denotes hydrogen and $R_5$ denotes methyl, then $R_4$ does not denote a hydrogen atom or a methyl or ethyl radical.

Among the compounds of formula (I) above, the ceramides and/or glycoceramides described by Downing in Journal of Lipid Research, Vol. 35, page 2060, 1994 or those described in French patent application FR-2,673,179, the disclosures of which are specifically incorporated herein by reference, are preferred.

The compounds of ceramide type more particularly preferred according to the invention are compounds of formula (I) for which $R_1$ denotes an optionally hydroxylated saturated or unsaturated alkyl radical derived from $C_{14}$–$C_{22}$, preferably $C_{16}$–$C_{22}$, fatty acids; $R_2$ denotes a hydrogen atom; and $R_3$ denotes an optionally hydroxylated, saturated, linear $C_{11}$–$C_{17}$, preferably $C_{13}$–$C_{15}$ and more preferably $C_{15}$, radical.

Such compounds are, for example:
2-N-linoleoylaminooctadecane-1,3-diol,
2-N-oleoylaminooctadecane-1,3-diol,
2-N-palmitoylaminooctadecane-1,3-diol,
2-N-stearoylaminooctadecane-1,3-diol,
2-N-behenoylaminooctadecane-1,3-diol,
2-N-[2-hydroxypalmitoyl]aminoactadecane-1,3-diol, 2-N-stearoylaminooctadecane-1,3,4-triol and in particular N-stearoylphytosphingosine,
2-N-palmitoylaminohexadecane-1,3-diol
or mixtures of these compounds.

Specific mixtures such as, for example, mixtures of ceramide(s) 2 and ceramide(s) 5 according to the Downing classification may also be used.

Compounds of formula (I) for which $R_1$ denotes a saturated or unsaturated alkyl radical derived from fatty acids; $R_2$ denotes a galactosyl or sulphogalactosyl radical; and $R_3$ denotes a saturated or unsaturated $C_{12}$–$C_{22}$ hydrocarbon radical and preferably a —CH=CH—(CH$_2$)$_{12}$—CH$_3$ group, may also be used.

Compounds of ceramide type are described, for example, in patent applications DE4,424,530, DE4,424,533, DE4,402,929, DE4,420,736, WO 95/23807, WO 94/07844, EP-A-0,646,572, WO 95/16665, FR-2,673,179, EP-A-0,227,994 and WO 94/07844, WO 94/24097 and WO 94/10131, the disclosures of which are specifically incorporated herein by reference.

By way of example, mention may be made of the product containing of a mixture of glycoceramides, sold under the trade name GLYCOCER by the company Waitaki International Biosciences.

The compounds described in patent applications EP-A-0,227,994, EP-A-0,647,617, EP-A-0,736,522 and WO 94/07844, the disclosures of which are specifically incorporated by reference herein, may also be used.

Such compounds are, for example, QUESTAMIDE H, also known as bis(N-hydroxyethyl-N-cetyl)malonamide and sold by the company Quest, and the N-(2-hydroxyethyl)-N-(3-cetyloxy-2-hydroxypropyl)amide of cetylic acid.

N-Docosanoyl-N-methyl-D-glucamine as described in patent application WO 94/24097, the disclosure of which is specifically incorporated by reference herein, and N-dodecasanoyl-N-methyl-D-glucamine as described in patent application WO 92/05764, the disclosure of which is specifically incorporated by reference herein, may also be used.

The compound of ceramide type used in the present invention is preferably chosen from N-oleoyldihydrosphingosine, N-2-hydroxypalmitoyl-dihydrosphingosine and N-stearoylphytosphingosine.

According to the invention, the content of ceramide-type compound may range from 0.01% to 10% by weight, and preferably from 0.1% to 1%, relative to the total weight of the composition.

The compound of ceramide type may be incorporated into the composition in powder form or in disperse form in water, an organic solvent such as isopropanol, or an oil.

Moreover, the cosmetic composition of the invention comprises a cosmetically acceptable support.

This support may comprise organic solvents, water, and/or is an oily medium, for example.

Organic solvents which may be mentioned are ketones such as acetone, methyl ethyl ketone and methyl isobutyl ketone; glycol ethers; alcohols such as ethanol, n-butanol, n-propanol and isopropanol; acetates such as butyl, ethyl or isopropyl acetate, or 2-methoxyethyl acetate; linear or branched hydrocarbons such as hexane or octane; or alternatively aromatic hydrocarbons such as xylene and toluene.

When the cosmetically acceptable support comprises water, the composition may be, in particular, in the form of an aqueous or aqueous-alcoholic solution, an oil-in-water or water-in-oil emulsion, or even a multiple emulsion, or alternatively in the form of an aqueous gel.

The oily medium may comprise one or more volatile and/or non-volatile oils, for example of plant, mineral, animal and/or synthetic origin, among which mention may be made of:

animal or plant oils formed by fatty acid esters or polyols, in particular liquid triglycerides, for example sunflower oil, corn oil, soya oil, marrow oil, grapeseed oil, sesame oil, hazelnut oil, apricot oil, almond oil or avocado oil, fish oils, glyceryl tricaprocaprylate, or plant or animal oils of formula $R_1COOR_2$ in which $R_1$ represents a higher fatty acid residue containing from 7 to 19 carbon atoms and $R_2$ represents a branched hydrocarbon chain containing from 3 to 20 carbon atoms, for example purcellin oil;

natural or synthetic essential oils such as, for example, eucalyptus oil, hybrid lavender oil, lavender oil, vetiver oil, lemon oil, sandalwood oil, rosemary oil, camomile oil, savory oil, nutmeg oil, cinnamon oil, hyssop oil, caraway oil, orange oil, geraniol oil, cade oil and bergamot oil;

hydrocarbons such as hexadecane and liquid paraffin;

inorganic acid esters of an alcohol;

ethers and polyethers;

silicone oils and gums.

In addition, the composition may comprise a film-forming polymer, which makes it possible to apply, for example, onto the nail a resistant film which ensures prolonged contact of the ceramide with the surface of the nail.

By way of example, the polymer may be chosen from nitrocellulose, cellulose acetobutyrate, polyvinyl butyrals, alkyd resins, polyesters, polyurethanes, polyester-polyurethanes, polyether-polyurethanes, radical polymers, in particular of acrylic, acrylic styrene and/or vinyl type and mixtures thereof.

The polymers may be dissolved or dispersed in the composition. They may generally be present at a content ranging from 1% to 40% by weight relative to the total weight of the composition.

The composition according to the invention may also comprise, in addition to the film-forming polymer, plasticizers which make it possible to adjust the flexibility of the film without lowering its physical strength.

The plasticizers which may be used are those commonly employed in nail varnish compositions. Plasticizers which may be mentioned are dibutyl, dioctyl, dilsobutyl and dimethoxyethyl phthalates, benzyl and glyceryl benzoates;

triethyl and tributyl citrates, acetyl tributyl citrate; tributyl and triphenyl phosphates; glycols; camphor and derivatives thereof and mixtures thereof. The plasticizers may generally be present at a content ranging from 1% to 30% by weight relative to the total weight of the composition.

The composition according to the invention may, in addition, comprise rheological agents. Rheological agents which may be mentioned are clays, pyrogenic silica, associative polymers of polyurethane type, cellulose derivatives and natural gums such as xanthan gum.

Moreover, the composition according to the invention may contain adjuvants commonly used in cosmetic compositions. Mention may be made, by way of example, of dye adjuvants, pigments, pearlescent agents, lakes, anti-UV agents, thickeners, surfactants, waxes, fragrances, active agents such as D-panthenol, phytanetriol, vitamins and derivatives thereof, keratin and derivatives thereof, melanin, collagen, cystine, chitosan and derivatives thereof, biotin, trace elements, glycerol, protein hydrolysates, phospholipids and moisturizers. Obviously, a person skilled in the art will care to select this or these optional adjuvants and/or the amount thereof such that the advantageous properties of the composition according to the invention are not, or are substantially not, adversely affected by the addition envisaged.

The composition according to the invention may be in the form of a nail varnish or a nail care composition.

Examples illustrating the present invention without, however, limiting it will now be given.

EXAMPLE 1

A shiny nail care base having the following composition was prepared:

| Nitrocellulose | 10 g |
|---|---|
| Resin and plasticizer | 15 g |
| N-Oleoyldihydrosphingosine | 0.5 g |
| Dyes and additives | 0.5 g |
| solvents (ethyl acetate, butyl acetate, isopropyl alcohol) | qs 100 g |

A shiny care base which was easily applied to the nail was thus obtained. This base made it possible, after drying, to obtain a smooth, uniform, shiny film.

EXAMPLE 2

A nail care base having the following composition could be prepared:

| Acrylic polymer in aqueous dispersion | 14 g |
|---|---|
| Polyurethane in aqueous dispersion | 13.5 g |
| N-Oleoyldihydrosphingosine | 0.5 g |
| Co-solvents (ethyl alcohol, isopropyl alcohol) | 6 g |
| Dyes and additives | 0.5 g |
| Water | qs 100 g |

When applied to the nails this care base should leave, after drying, a smooth, shiny, uniform film.

EXAMPLE 3

A nail care base having the following composition was prepared:

| Plant oil | 2 g |
|---|---|
| N-Oleoyldihydrosphingosine | 0.5 g |
| Volatile silicone oil | 87.5 g |
| Solvents (ethyl alcohol, isobutyl alcohol) | 10 g |

A nail care oil was thus obtained which, after application, deposited a protective film on the nail. The film penetrated by massaging into the matrix and the nail bed.

EXAMPLE 4

A shiny nail care base having the following composition was prepared:

| Nitrocellulose | 10 g |
|---|---|
| Resin and plasticizer | 15 g |
| N-2-Hydroxypalmitoyldihydrosphingosine | 0.5 g |
| Dyes and additives | 0.5 g |
| Solvents (ethyl acetate, butyl acetate, isopropyl alcohol) | qs 100 g |

A shiny care base which was easily applied to the nail was thus obtained. This base made it possible, after drying, to obtain a smooth, uniform, shiny film.

EXAMPLE 5

A nail care base having the following composition was prepared:

| Plant oil | 2 g |
|---|---|
| N-oleoyldihydrosphingosine | 0.47 g |
| N-2-hydroxypalmitoyldihyrosphingosine | 0.02 g |
| N-stearoylphytosphingosine | 0.01 g |
| Volatile silicone oil | 87.5 g |
| Solvents (isopropyl alcohol) | 10 g |

A nail care oil which, after application, deposited a protective film on the nail was thus obtained. The film penetrated by massaging into the nail matrix and the nail bed. The nail treated with the care oil became smooth and shiny. The surface of the nail thus treated became uniform.

EXAMPLE 6

A nail care base having the following composition was prepared:

| Plant oil | 2 g |
|---|---|
| N-oleoyldihydrosphingosine | 0.4 g |
| N-2-hydroxypalmitoyldihyrosphingosine | 0.1 g |
| Isopropyl alcohol | 10 g |
| Volatile silicone oil | qs 100 g |

A nail care oil which, after application, deposited a protective film on the nail was thus obtained. The film penetrated by massaging into the nail matrix and the nail bed. The nail treated with the care oil became smooth and shiny. The surface of the nail thus treated became uniform.

I claim:

1. A process for making the outer surface of nails uniform, comprising the step of applying to the nails a nail varnish comprising at least one ceramide compound in a concentration effective to make the outer surface of the nails uniform, at least one film-forming polymer, and an alcohol solvent.

2. A process according to claim 1, wherein said process improves the smoothness of the outer surface of the nails.

3. A process according to claim 1, wherein said process improves the shininess of the outer surface of the nails.

4. A process according to claim 1, wherein said at least one ceramide compound is a compound of formula (I):

$$R_1-\underset{\underset{O}{\|}}{C}-\underset{\underset{R_4}{|}}{N}-\underset{\underset{R_5}{|}}{CH}-CH-O-R_2 \quad \text{(I)}$$
$$\qquad\qquad\qquad\qquad R_3$$

wherein:

$R_1$ denotes:
either a saturated or unsaturated, linear or branched $C_1-C_{50}$ hydrocarbon radical, it being possible for this radical to be substituted with one or more hydroxyl groups which are optionally esterified with an acid $R_7COOH$, $R_7$ being an optionally mono- or polyhydroxylated linear or branched, saturated or unsaturated $C_1-C_{35}$ hydrocarbon radical, it being possible for the hydroxyl or hydroxyls of the radical $R_7$ to be esterified with an optionally mono- or polyhydroxylated, linear or branched, saturated or unsaturated $C_1-C_{35}$ fatty acid, or a radical R"—(NR—CO)—R', wherein R denotes a hydrogen atom or a mono- or polyhydroxylated $C_1-C_{20}$ hydrocarbon radical, and R' and R" are hydrocarbon radicals, the sum of whose carbon atoms ranges from 9 to 30, R' being a divalent radical, or a radical $R_8$—O—CO—$(CH_2)_p$, wherein $R_8$ denotes a $C_1-C_{20}$ hydrocarbon radical, and p is an integer ranging from 1 to 12;

$R_2$ is chosen from a hydrogen atom, a radical of saccharide type, a sulphate or phosphate residue, a phosphorylethylamine radical and a phosphorylethylammonium radical;

$R_3$ denotes a hydrogen atom or a $C_1-C_{33}$, saturated or unsaturated, hydroxylated or non-hydroxylated hydrocarbon radical, it being possible for the hydroxyl or hydroxyls to be esterified with an inorganic acid or an acid $R_7COOH$, $R_7$ having the same meanings as above, it being possible for the hydroxyl or hydroxyls to be etherified with a (glycosyl)$_n$, (galactosyl)$_m$, wherein n is an integer ranging from 1 to 4 and m is an integer ranging from 1 to 8, sulphogalactosyl, phosphorylethylamine or phosphorylethylammonium radical, it also being possible for $R_3$ to be substituted with one or more $C_1-C_{14}$ alkyl radicals;

$R_4$ denotes a hydrogen atom, a methyl or ethyl radical, an optionally hydroxylated linear or branched, saturated or unsaturated $C_3-C_{50}$ hydrocarbon radical or a radical —$CH_2$—CHOH—$CH_2$—O—$R_6$ in which $R_6$ denotes a $C_{10}-C_{26}$ hydrocarbon radical or a radical $R_8$—O—CO—$(CH_2)_p$, $R_8$ denotes a $C_1-C_{20}$ hydrocarbon radical, and p is an integer ranging from 1 to 12; and $R_5$ denotes a hydrogen atom or an optionally mono- or polyhydroxylated linear or branched, saturated or unsaturated $C_1-C_{30}$ hydrocarbon radical, it being possible for the hydroxyl or hydroxyls to be etherified with a (glycosyl)$_n$, (galactosyl)$_m$, wherein n and m are as defined above for $R_3$, sulphogalactosyl, phosphorylethylamine or phosphorylethylammonium radical, with the proviso that when $R_3$ and $R_5$ denote hydrogen or when $R_3$ denotes hydrogen and $R_5$ denotes methyl, then $R_4$ does not denote a hydrogen atom or a methyl or ethyl radical.

5. A process according to claim 4, wherein in $R_1$ said saturated or unsaturated, linear or branched $C_1-C_{50}$ hydrocarbon radical is a $C_5-C_{50}$, hydrocarbon radical; wherein in said radical R"—(NR—CO)—R', R denotes a monohydroxylated $C_1-C_{20}$ hydrocarbon radical; and wherein in $R_2$ said radical of saccharide type is selected from a (glycosyl)$_n$, a (galactosyl)$_m$ and a sulphogalactosyl radical, in which n is an integer ranging from 1 to 4 and m is an integer ranging from 1 to 8.

6. A process according to claim 4, wherein said at least one ceramide compound is a compound of formula (I) in which $R_1$ denotes either a saturated or unsaturated, linear or branched $C_9-C_{30}$ hydrocarbon radical, it being possible for this radical to be substituted with one or more hydroxyl groups, these hydroxyl groups optionally being esterified with a saturated or unsaturated $C_{16}-C_{30}$ fatty acid; or a radical R"—(NR—CO)—R', where R denotes a hydrogen atom or a mono- or polyhydroxylated $C_1-C_{10}$ hydrocarbon radical, R' and R" are hydrocarbon radicals, the sum of whose carbon atoms ranges from 9 to 30, R' being a divalent radical;

$R_2$ denotes a hydrogen atom or a (glycosyl)$_n$, (galactosyl)$_m$ or sulphogalactosyl radical, in which n is an integer ranging from 1 to 4 inclusive and m is an integer ranging from 1 to 8 inclusive;

$R_3$ denotes a hydrogen atom or a saturated or unsaturated $C_{16}-C_{27}$ hydrocarbon radical, it being possible for this radical to be substituted with one or more $C_1-C_{14}$ alkyl radicals; $R_3$ may also denote a $C_{15}-C_{26}$ α-hydroxyalkyl radical in which the hydroxyl group may optionally be esterified with an $C_{16}-C_{30}$ α-hydroxy acid;

$R_4$ denotes a hydrogen atom, a saturated or unsaturated $C_{16}-C_{27}$ hydrocarbon radical or a radical —$CH_2$—CHOH—$CH_2$—O—$R_6$ in which $R_6$ denotes a $C_{10}-C_{26}$ hydrocarbon radical; and $R_5$ denotes a hydrogen atom or a mono- or polyhydroxylated $C_1-C_4$ hydrocarbon radical.

7. A process according to claim 6, wherein in said radical R"—(NR—CO)—R', R denotes a mono-hydroxylated $C_1-C_{10}$ hydrocarbon radical.

8. A process according to claim 4, wherein said at least one ceramide compound is a compound of formula (I) in which $R_1$ denotes an optionally hydroxylated saturated or unsaturated alkyl radical derived from $C_{16}-C_{22}$ fatty acids;

$R_2$ denotes a hydrogen atom; and $R_3$ denotes an optionally hydroxylated, saturated, linear $C_{15}$ radical.

9. A process according to claim 8, wherein said at least one ceramide compound is selected from:
N-linoleoyldihydrosphingosine,
N-oleoyldihydrosphingosine,
N-palmitoyldihydrosphingosine,
N-stearoyldihydrosphingosine,
N-behenoyldihydrosphingosine, N-2-hydroxypalmitoyldihydrosphingosine, and
N-stearoylphytosphingosine.

10. A process according to claim 9, wherein said at least one ceramide compound is selected from N-oleoyldihydrosphingosine, N-2-hydroxypalmitoyldihydrosphingosine and N-stearoylphytosphingosine.

11. A process according to claim 1, wherein said at least one ceramide compound is present in a concentration ranging from 0.01% to 10% by weight, relative to the total weight of said cosmetic composition.

12. A process according to claim 11, wherein said at least one ceramide compound is present in a concentration ranging from 0.1% to 1% by weight, relative to the total weight of said cosmetic composition.

13. A process according to claim 1, wherein said at least one film-forming polymer is selected from nitrocellulose, cellulose acetobutyrate, polyvinyl butyrals, alkyd resins, polyesters, acrylics and polyurethanes.

14. A process according to claim 1, wherein said cosmetic composition additionally comprises at least one plasticizer.

15. A process according to claim 1, wherein said cosmetic composition is in the form of a nail varnish or a nail care composition.

16. A process for making the outer surface of nails uniform according to claim 1, wherein said nail varnish further comprises a cosmetically acceptable support comprising at least one oil.

17. The process of claim 1, wherein said alcohol solvent is isopropyl alcohol.

18. The process of claim 1 wherein said alcohol solvent is ethyl alcohol.

19. The process of claim 1 wherein said alcohol solvent is a mixture of isopropyl alcohol and ethyl alcohol.

* * * * *

UNITED STATES PATENT AND TRADEMARK OFFICE
CERTIFICATE OF CORRECTION

PATENT NO.     : 6,099,826
DATED          : August 8, 2000
INVENTOR(S)    : Roland Ramin It is certified that error appears in the above-identified patent and that said Letters Patent is hereby corrected as shown below:

Title page,
Item [22], "Filed: Jul. 21, 1997" should read -- Filed: April 21, 1997 --.

Signed and Sealed this

Eighteenth Day of September, 2001

Attest:

NICHOLAS P. GODICI
Attesting Officer
Acting Director of the United States Patent and Trademark Office